United States Patent [19]

Sausa

[11] Patent Number: 5,759,859
[45] Date of Patent: Jun. 2, 1998

[54] SENSOR AND METHOD FOR DETECTING TRACE UNDERGROUND ENERGETIC MATERIALS

[75] Inventor: Rosario C. Sausa, Bel Air, Md.

[73] Assignee: United States of America as represented by the Secretary of the Army, Washington, D.C.

[21] Appl. No.: 680,080

[22] Filed: Jul. 15, 1996

[51] Int. Cl.$^6$ ................................................. G01N 33/22
[52] U.S. Cl. ................... 436/106; 73/152.11; 73/152.23; 73/152.46; 436/28; 436/118; 436/149; 436/172
[58] Field of Search ................. 436/106, 28, 116–118, 436/149, 164, 172; 422/82.05–82.11, 82.01; 73/152.11, 152.23, 152.46

[56] References Cited

U.S. PATENT DOCUMENTS

| | | | |
|---|---|---|---|
| 5,094,815 | 3/1992 | Conboy et al. | |
| 5,123,274 | 6/1992 | Carroll et al. | |
| 5,128,882 | 7/1992 | Cooper et al. | |
| 5,246,862 | 9/1993 | Grey et al. | 436/28 |
| 5,316,950 | 5/1994 | Apitz et al. | |
| 5,351,532 | 10/1994 | Hager | 436/28 |
| 5,364,795 | 11/1994 | Sausa et al. | |

OTHER PUBLICATIONS

Chemical Abstracts CA 124:210801, Wormhoudt et al., Mater Res. Soc. Symp. Proc. (1996), 418 (Decomposition, Combustion and Detonation Chemistry of Energetic Materials), pp. 143–148, 1996.

Chemical Abstracts CA 124:163604, Theriault et al., Proc. SPIE–Int. Soc. Opt. Eng. (1995), 2504 (Environmental Monitoring and Hazardous Waste Site Remediation, 1995), pp. 75–83, 1995.

Theriault et al., Field deployment of a LIBS probe for rapid delineation of metals in soils, Proc. SPIE–Int. Soc. Opt. Eng. (1996), 2835(Advanced Technologies for Environmental Monitoring and Remediation), 83–88, Aug. 1996.

Wormhoudt et al., Tunable infrared laser detection of pyrolysis products of explosives in soils, Appl. Opt. (1996), 35(21), 3992–3997, Jul. 1996.

Bratton et al., Site characterization using optical sensors and cone penetrometers, Proc. SPIE–Int. Soc. Opt. Eng. (1996), 2883(Optical Remote Sensing for Environmental and Process Monitoring), 596–607, Sep. 1995.

Nielsen et al., A new site characterization and monitoring technology, Proc. SPIE–Int. Soc. Opt. Eng. (1995), 2504(Environmental Monitoring and Hazardous Waste Site Remediation, 1995), 278–291, Jun. 1995.

Theriault et al., Remote in–situ detection of heavy metal contamination in soils using a fiber optic laser induced breakdown spectroscopy (FOLIBS) system, Proc. SPIE–Int. Soc. Opt. Eng. (1995), 2540(Environmental Monitoring and Hazardous Waste Site Remedi, Jun. 1995.

Wormhoudt et al., Studies of pyrolysis products of explosives in soils using infrared tunable diode laser detection, Mater. Res. Soc. Symp. Proc. (1996), 418(Decomposition, Combustion, and Detonation Chemistry of Energetic Materials), 143–148, 1996.

Dimicoli et al., SPIE vol. 669 Laser Application in Chemistry (1986), pp. 40–45, 1986.

*Primary Examiner*—Jan Ludlow
*Attorney, Agent, or Firm*—Paul S. Clohan; Muzio B. Roberto

[57] ABSTRACT

A subsurface soil contaminant identification system employs a cone penetrometer unit for continuously measuring the concentration of energetic materials in potentially contaminated soils. The sensor is rugged, reliable, and has a fast response time. The invention utilizes two pulsed, time-delayed miniature lasers. An infrared laser is used for decomposing the energetic material into NO and other products, while a visible laser operating near 452 nm is used for NO detection by (2+2) resonance-enhanced multiphoton ionization (REMPI). The system employs a fiber optic to transmit the output radiation at distances of approximately 30–50 meters, a lens assembly to focus one or both laser beams, a pair of miniature electrodes to collect the ions, a penetrometer, and data acquisition/processing equipment. A REMPI spectrum of 0.1% NO at atmospheric pressure reveals that the spectral resolution is sufficient such that characteristic spectral features of NO can be identified unequivocally.

8 Claims, 7 Drawing Sheets

NITROGLYCERINE

PENTAERYTRITOL TETRANITRATE

RDX

HMX

TNT

DATB

SENSOR AND METHOD FOR DETECTING TRACE UNDERGROUND ENERGETIC MATERIALS

FIELD OF THE INVENTION

This invention is directed to a device and method for real-time, in situ detection of trace energetic materials including propellants and explosives in subsurface soil.

RELATED APPLICATIONS

The disclosure of this application is hereby incorporated by reference.

DESCRIPTION OF THE RELATED ART

In recent years there has been a growing interest in the development of fast, sensitive, and cost effective devices for monitoring subsurface contaminants such as petroleum oil, chlorinated solvents, heavy metals, and energetic materials. Most of this interest stems from environmental issues related to pollution prevention, compliance, cleanup, and restoration.

A common technique for subsurface site characterization and analysis utilizes a cone penetrometer system equipped with a gas chromatograph coupled to a mass spectrometer (GC/MS). The penetrometer system consists of a truck equipped with a vertical hydraulic ram that is used to force a rod with umbilical cord into the ground at a depth up to 30 meters. A suction device mounted near the rod allows sample vapors from the soil to be transported via a small diameter tube to the analysis chamber for GC/MS analysis onboard the truck. As the rod is pushed or retrieved from the ground a vertical profile of soil condition as a function of height below ground surface is obtained. Repeated vertical profiling at various locations results in a three dimensional mapping of the potentially contaminated site. This system is quite effective at monitoring many pollutants as GG/MS spectrometry has a high degree of sensitivity and selectivity. However, the sensor is relatively slow since each chromatograph and mass spectrograph recorded for a particular point in the vertical profile requires tens of minutes to acquire. In this system the sample must be extracted and transported several tens of meters to the analysis chamber. This process further delays data acquisition for stable species and is not effective for reactive contaminants.

U.S. Pat. No. 5,128,882 to Cooper and Malone discloses a device and method for measuring reflectance and fluorescence of in-situ soil. Their invention consists of a cone penetrometer system in which the probe is fitted with a light transparent window and a light source disposed internally of the probe. Light passes through the transparent window and is absorbed by the contaminant in the soil. The resulting fluorescence is transmitted from the contaminant back through the window onto a fiber optic cable. Light reflected by the contaminant can also be measured. In either case, the fluorescence or reflection signal is transmitted through the fiber to the surface for analysis. Determination of the type and amount of contaminant is possible by comparison of the spectral signature of the soil to standards prepared by adding known concentrations of specific contaminant to soil similar to the soil found on the test site.

U.S. Pat. No. 5,316,950 to Apitz et al teach a method for quantitative calibration of in situ optical measurements in soils using soil class characteristics. This method and the technique of Cooper and Malone are utilized for the detection of petroleum oil or lubricants, and cannot be used for soil contaminated with non fluorescent or weakly fluorescent species such as many energetic materials.

More recently, Miles, Cooper, Cespedes, and Therinult disclose a method and apparatus for in situ elemental identification of soil contaminants; see U.S. Corps of Engineers, Case No. COE-350. The system utilizes a cone penetrometer and is based on laser-induced breakdown spectrometry (LIBS). Unlike the fluorescence penetrometer system, the LIBS based system requires large laser fluxes to induce dielectric breakdown of the soil contaminants. The output of a Nd:YAG laser onboard a truck is transmitted to the cone tip of the penetrometer by means of an optical fiber and focused onto contaminated soil through a sapphire window. The plasma generated by the focused radiation results in the dissociation of most molecular species yielding electronically excited atomic fragments which emit characteristic radiation as they decay to their ground electronic state. The emission signal, as in the case of the fluorescence based system, is then transmitted by an optical fiber to a spectrometer photodetector system onboard the truck. Although this system is capable of in situ and real-time analysis of contaminated soil, it is limited to metallic species such as mercury, lead, or chromium. The dielectric breakdown of energetic materials results in the production of nitrogen and oxygen atoms which could not be discriminated from air and/or soil breakdown.

An electrochemical sensor for detecting subsurface explosive contaminants is also known. A heater unit mounted inside the penetrometer is used to pyrolyze the energetic material imbedded in the soil into NO and other products. The NO vapors are then collected through the penetrometer inlet ports, as air is continuously swept through the output ports, and directed over the sensor for analysis. Subsequent to analysis, the vapors are drawn to the surface where they are vented outside the truck. In the analysis unit of the penetrometer, NO is detected electrochemically by the reaction, $NO+H_2O=NO_2+2H^++2e^-$. The sensor was demonstrated at the Louisiana Army Ammunition Plat in September, 1994, with an overall favorable field performance. Limitations of the system include: (1) relatively low sensitivity (low ppm), (2) problems with interferant compounds which can also produce similar electrochemical signals, thus questioning the validity of the measurement, and (3) large amount of time required for each measurement (minutes). The latter is due to the time required to eliminate/reduce memory effects of a previous run and slow heating/cooling cycle of the pyrolyzing unit.

Recently, Sausa and coworkers of the U.S. Army Research Laboratory have utilized the Laser Photofragmentation/Fragment Detection method to detect trace nitrocompounds including energetic materials. Selected references include: (1) Sausa, Simeonsson, and Lemire, "A laser-based method for detecting nitrocompounds", U.S. Pat. No. 5,364,795, and (2) Simeonsson, Lemire, and Sausa, "Trace detection of nitrocompounds by ArF laser photofragmentation/ionization spectrometry", *Applied Spectroscopy*, Vol. 47, No. 11, p. 190 (1993). The technique utilizes one laser operating at 226 or 193 nm to both photofragment the target molecule and facilitate detection of the characteristic NO photofragment. Using a laser operating near 226 nm, NO is detected by resonance-enhanced multiphoton ionization (REMPI) or laser induced fluorescence (LIF) via its $A^2\Sigma-X^2\Pi$ transitions near 226 nm. In another case, using an ArF laser, NO is detected by REMPI processes via the NO $A^2\Sigma-X^2\Pi$ (3,0), $B^2\Pi-X^2\Pi$ (7,0), and $D^2\Sigma-X^2\Pi$ (1,0) bands at 193 nm. In both cases, the analytical utility is demonstrated for several compounds using a molecular beam time-of-flight mass spectrometry with limits of detection in the low ppb to ppm range. Although the sensor has a high sensitivity and fast response, its utility in the field is limited due to the size of the mass spectrometer. In addition, the 193 and 226 nm radiation cannot be transmitted by an optical fiber cable with significant energies at distances of 20–30 m. Also, the sample needs to be retrieved over long distances, thus introducing problems associated with memory effects and reactions of the photofragments.

More recently, Simeonsson, Lemire, and Sausa published an article titled, "Laser-induced photofragmentation/ photoionization spectrometry: A method for detecting ambient oxides of nitrogen," *Analytical Chemistry*, Vol. 66, No. 14, p. 2272, 1994. In this method, a tunable laser operating near 226 nm is used for fragmentation and also for ionizing the characteristic NO fragment. The charged particles which are generated are then collected using a pair of miniature electrodes. A limitation of this technique for subsurface characterization is that the 226 nm laser radiation is attenuated appreciably by a relatively long optical fiber.

At present, there are a number of DoD sites that are contaminated with various pollutants, including energetic materials, and require site characterization for cleanup and/ or remediation measures. As current technology has the limitations noted above, there is a need for new technology.

SUMMARY OF THE INVENTION

An object of the invention is to provide a method and apparatus for subsurface analysis of contaminated soil with energetic materials.

Another object of the invention is to provide a sensor and method capable of performing such analysis in real time and in situ.

Yet another object is to provide such a sensor which is rugged, accurate and reliable and which has a fast response time.

To achieve these and other objects, the present invention is directed to a detection and monitoring system comprising a penetrometer unit, two miniature lasers coupled to an optical fiber which terminates near the rod head, a pair of miniature electrodes mounted inside or external to the penetrometer, optical ports, lens assembly, current amplifier, boxcar averager, digital oscilloscope, and a computer (e.g., laptop) for data acquisition and analysis. The lasers are time-delayed pulsed lasers, one operating in the infrared (IR) and the other in the visible portion of the spectrum, preferably near 452 nm.

The invention is further directed to a method for using the sensor described above. The IR laser radiation is used to pyrolyze the energetic material in the soil to produce No vapors, while the visible laser radiation is used to ionize the NO by a (2+2) resonance-enhanced ionization process. The charged particles are collected by a pair of miniature electrode, and the resultant signal amplified and directed to an analysis unit onboard a truck.

The present invention is directed to a subsurface soil contaminant identification system employing a penetrometer unit for continuously measuring the concentration of energetic materials in potentially contaminated soils. The sensor is rugged, reliable, and has a fast response time. The invention utilizes two pulsed, time-delayed miniature lasers (i.e., the pulses which are emitted by one laser are time-delayed relative to the pulses of the other laser). An infrared laser is used for decomposing the energetic material into NO and other products, while a visible laser operating near 452 nm is used for NO detection by (2+2) resonance-enhanced multiphoton ionization (REMPI). Also utilized in the present invention is a fiber optic to transmit the output radiation at distances of approximately 30–50 meter, a lens assembly to focus one or both laser beams, a pair of miniature electrodes to collect the ions, a penetrometer, and data acquisition/ processing equipment. A REMPI spectrum of 0.1% NO at atmospheric pressure reveals that the spectral resolution is sufficient such that characteristic spectral features of NO can be identified unequivocally. Calculations of surface temperature of sandstone with trace energetic materials as a function of laser fluence (a measure of laser intensity on a surface whose units are $J/cm^2$) reveal that the decomposition temperature of the energetic material to yield NO can be achieved with modest laser energies which are obtainable from commercially available lasers.

Laser-induced fluorescence and resonance-enhanced ionization techniques can at times provide very specific and sensitive methods of detection for many atomic and molecular systems. However, large molecules such as energetic materials are difficult to detect spectroscopically in the ultraviolet-visible (UV-VIS) region because they posses weak transitions or broad and poorly defined spectral features. In addition, many such molecules predissociate with the absorption of UV radiation, thus closing or minimizing channels for fluorescence or ionization. Thermal decomposition of large molecules results in the formation of characteristic fragments such as atoms and small molecules (e.g. diatomic and triatomic species) which can be generally detected by resonance-enhanced ionization since they possess a favorable combination of optical transitions which are usually strong and spectral features which are sharp and well-resolved.

The thermal decomposition of energetic materials such as 1,3,5-trinitrohexahydro-s-triazine (RDX) and octahydro-1, 3,5,7-tetranitro-1,3,5,7-tetrazocine (HMX) has been studied extensively in past years. For a partial list of references, see (1) J. C. Oxley, A. B. Kooh, R. Szekeres, and W. Zheng, "Mechanisms of nitramine thermolysis", *J. Phys. Chem.*, Vol. 98, p. 7004, 1994. (2) R. Behrens and S. Bulusu, "Thermal decomposition of energetic materials. 3. Temporal behaviours of the rates of formation of the gaseous pyrolysis products from the condensed phase decomposition of 1,3, 5-trinitrohexahydro-s-triazine", *J. Phys. Chem.*, Vol. 96, p. 8877, 1992. (3) R. Behrens and S. Bulusu, "Thermal decomposition of energetic materials. 4. Deuterium isotope effects and isotopic scrambling (H/D, $^{13}C/18O$, $^{14}N/^{15}N$) in condensed phase decomposition of 1,3,5 trinitrohexahydro-s-triazine, *J. Phys., Chem.*, Vol. 96, p. 8891, 1992. (4) M. A. Schroeder, "Critical analysis of nitramine decomposition data: Product distribution from HMX and RDX", BRL Technical Report: BRL-TR2673, 1985, (5) Y. Oyumi and T. B. Brill, "Thermal decomposition of energetic materials 3: A high-rate in situ, FTIR study of the thermolysis of RDX and HMX with pressure and heating rates as variables", *Combustion and Flame*, Vol. 62, p. 213, 1985, (6) T. L. Boggs, "The thermal decomposition behavior of RDX and HMX" in "Fundamental of Solid-Propellant Combustion, K.K. Kuo and M. Summerfield eds.; *Progress in Astronautics and Aeronautics*, Vol. 90, p. 121, AIAA Inc., New York, 1984, and (7) T. B. Brill, P. J. Brush, D. G. Patil, and J. K. Chen, "Chemical pathways at a burning surface", 24th *Symposium (international) on Combustion, The Combustion Institute*, p. 1907, 1992. Although the mechanisms operative in the thermal decomposition of RDX and HMX are not completely understood, there is general agreement that NO is a common end product of these compounds. Employing Simultaneous Thermogravity and Molecular Beam Mass Spectrometry (STMBMS), Behrens and Bulusu observed NO and other products from the isothermal decomposition of 10–30 mg of HMX at temperature between 200° and 250° C. using an alumina cell with a 50–100 μm diameter office. They also monitored RDX decomposition products using a thermal ramp technique with a heating rate of 1° C./min over a temperature range of 190°–210° C.

Brill et al have studied the decomposition of RDX and HMX using Fast Thermolysis-Fourier Transform Infrared Spectrometry (FT-FTIR). Various decomposition products such as $CO_2$, $N_2O$, $NO_2$, and HONO were identified when 2 mg of RDX was heated under 15 psi $N_2$ at a rate dT/dt–170° C./sec in about 1.15 sec. This corresponds to a temperature of approximately 200° C. which is agreement with the onset decomposition temperature of Behrens and Bulusu. Their results reveal that the NO concentration is negligible at the onset of RDX decomposition, but increases with time at the expense of $NO_2$, the dominant early decomposition product. NO can readily be observed at a decomposition time of 1.85 seconds, corresponding to a temperature of approximately 315° C.

The above-mentioned techniques have provided important information pertaining to product identification and mechanisms involved in the thermal decomposition of energetic materials. However, they are limited for field use since the instruments are relatively large, the process for thermal decomposition is relatively slow (seconds) and the samples must be retrieved for analysis. The present invention circumvents these problems because it utilizes two miniature lasers; one for decomposing the energetic material in the soil and the other for NO ionization.

The heating of a solid by a combination of convective and radiative inputs was treated by Boehringer and Spindler in a paper titled, "Radiant Heating of Semitransparent Materials", published in AIAA, Vol. 1, p. 84, 1963. The surface temperature of a material under the influence of a pure radiative flux is given by:

$$T(t)=T_o+2F(t)t^{1/2}/(\pi Cpk)^{1/2} \quad (1)$$

where T(t) is the temperature at time t, F(t) is the flux, $T_o$ is the initial temperature of the surface, C is the heat capacity, p is the density, and k is the thermal conductivity.

For soil composed of sandstone, C=0.26 cal/g.deg, p=2.2 g/cm³, and k=0.01 cal/sec.cm.deg (Handbook of Chemistry and Physics, 66th Edition, R. Weast ed., CRC Press, New York, 1985–86). Using a laser pulse duration of 1 μsec and assuming the soil temperature before irradiation is 25° C., the flux needed to heat the surface to a temperature in which an appreciable amount of NO is generated from energetic materials, typically 315° C. for RDX, is approximately $8\times10^4$ J/cm².sec. This value corresponds to a laser fluence of 80 mJ/cm². The above calculation also assumes that all of the laser energy is absorbed by the surface. This assumption is valid for an infrared laser with output near 10 μm, but not for a laser operating near 1 μm. For the latter, if the soil absorbs 10% of the laser radiation, then the fluence required to reach the same surface temperature would be approximately 0.8 J/cm². The fluences obtained from both calculations are certainly within the laser energy specifications of commercially available infrared lasers.

The present invention is used in the following fashion. Two miniature pulsed lasers with infrared and visible output are used for pyrolysis and NO ionization, respectively. The two lasers are mounted on a truck and the output beams are directed into a fiber optic which transmits the radiation to an optical port near the tip of a cone penetrometer. The IR laser radiation serves to pyrolyze the energetic material contaminant in the soil. As the pulse is hot, and is in the range of micro- to nanoseconds, pyrolysis of the energetic material occurs instantaneously producing copious quantities of NO vapors along with other products. The visible laser is then used to ionize NO by a (2+2) REMPI process near 452 nm. A pair of miniature collection plates mounted external or inside the cone penetrometer are used to collect the charged particles. The ion current produced is then converted to voltage by a transimpedance amplifier and then directed onboard a truck into a gated integrator or a digital oscilloscope for real-time display. A laptop computer or other suitable computing device interfaced to the boxcar or oscilloscope is used for data acquisition and analysis.

DETAILED DESCRIPTION OF THE PREFERRED EMBODIMENT

Figure 1:
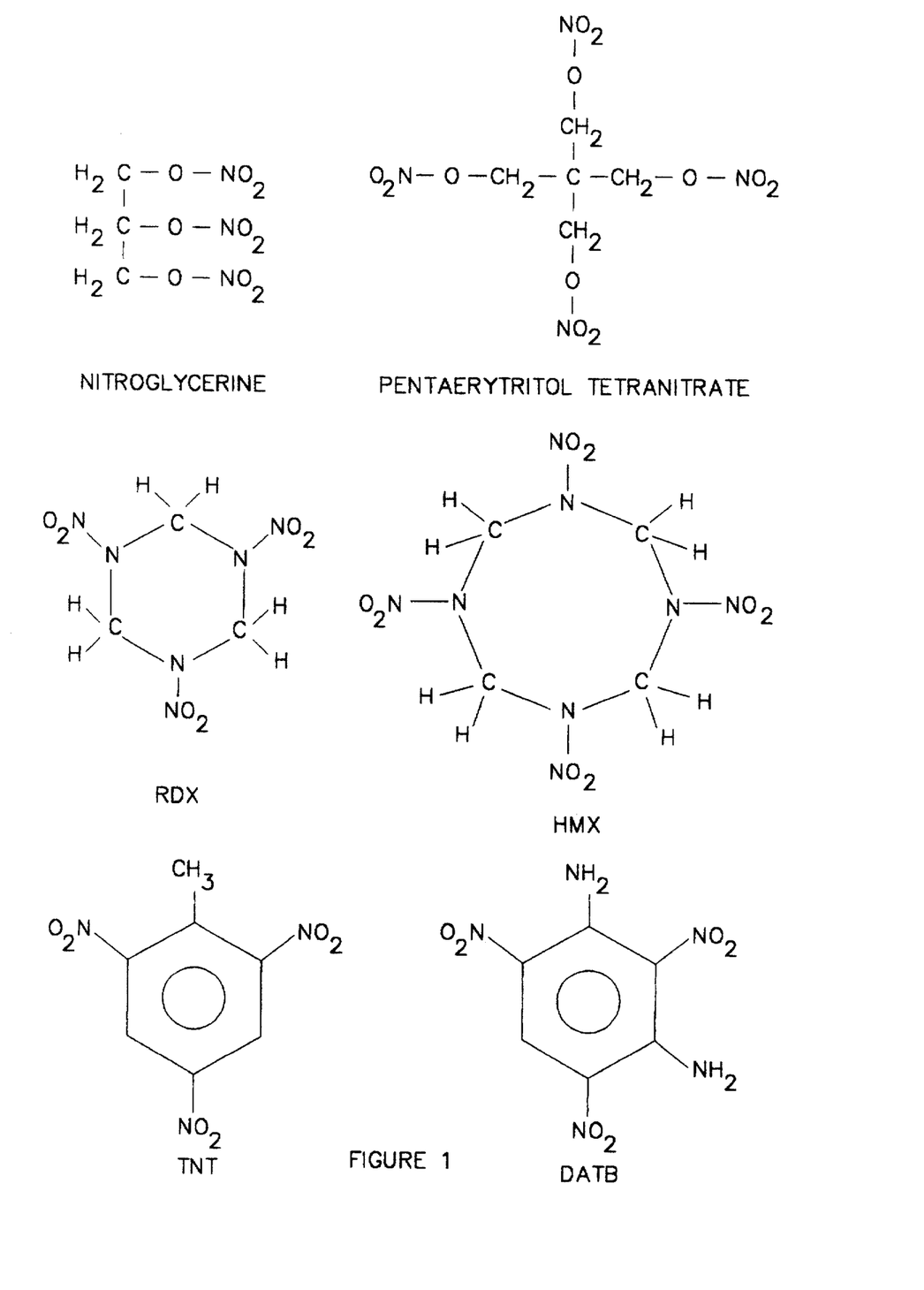
FIG. 1 shows the molecular structures of selected energetic compounds.

FIG. 1 is a table of selected energetic compounds. As shown in FIG. 1, all of the compounds contain the $NO_2$ moiety, which can easily be detached from the main skeletal portion of the molecule and decomposed to NO with infrared laser radiation. It should be noted that the mechanism for decomposition involves pyrolysis, as compared to photolysis, which would occur if the energetic material were excited with ultraviolet laser radiation. The latter would not be effective for subsurface cone penetrometer applications using fiber optics cables, since these cables could not transmit the laser radiation at distances of 30–50 m, commonly required for such applications. Laser pyrolysis is distinct from conventional pyrolysis, e.g. using a heater coil, in that the time for decomposition of the energetic material is very short, i.e., the duration of the laser pulse (microseconds).

Figure 2:
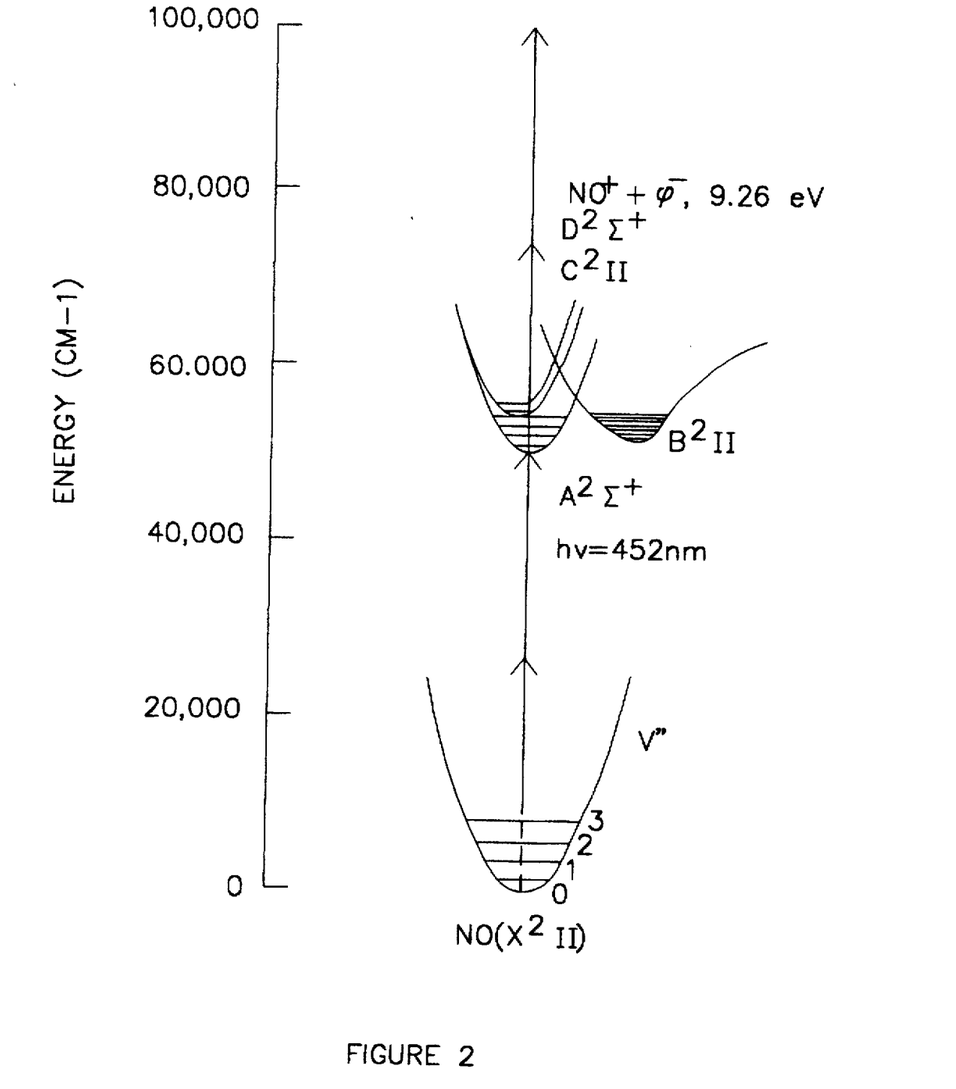
FIG. 2 shows a potential energy diagram of NO.

FIG. 2 is a partial potential energy diagram of NO adapted from Herzberg, *Molecular Spectra and Molecular Structure: I. Spectra of Diatomic Molecules*; Van Nostrand, Princeton, 1950. As shown in the diagram, NO is easily ionized at 9.26 eV by the absorption of visible laser radiation near 452 nm by a (2+2) REMPI ionization process via the intermediate $A^2\Sigma^+$ state. Other ro-vibrational energy levels of the electronic A state may also be used to achieve ionization. In addition, the electronic B, C, and D states also serve as intermediates for ionization.

Figure 3A:
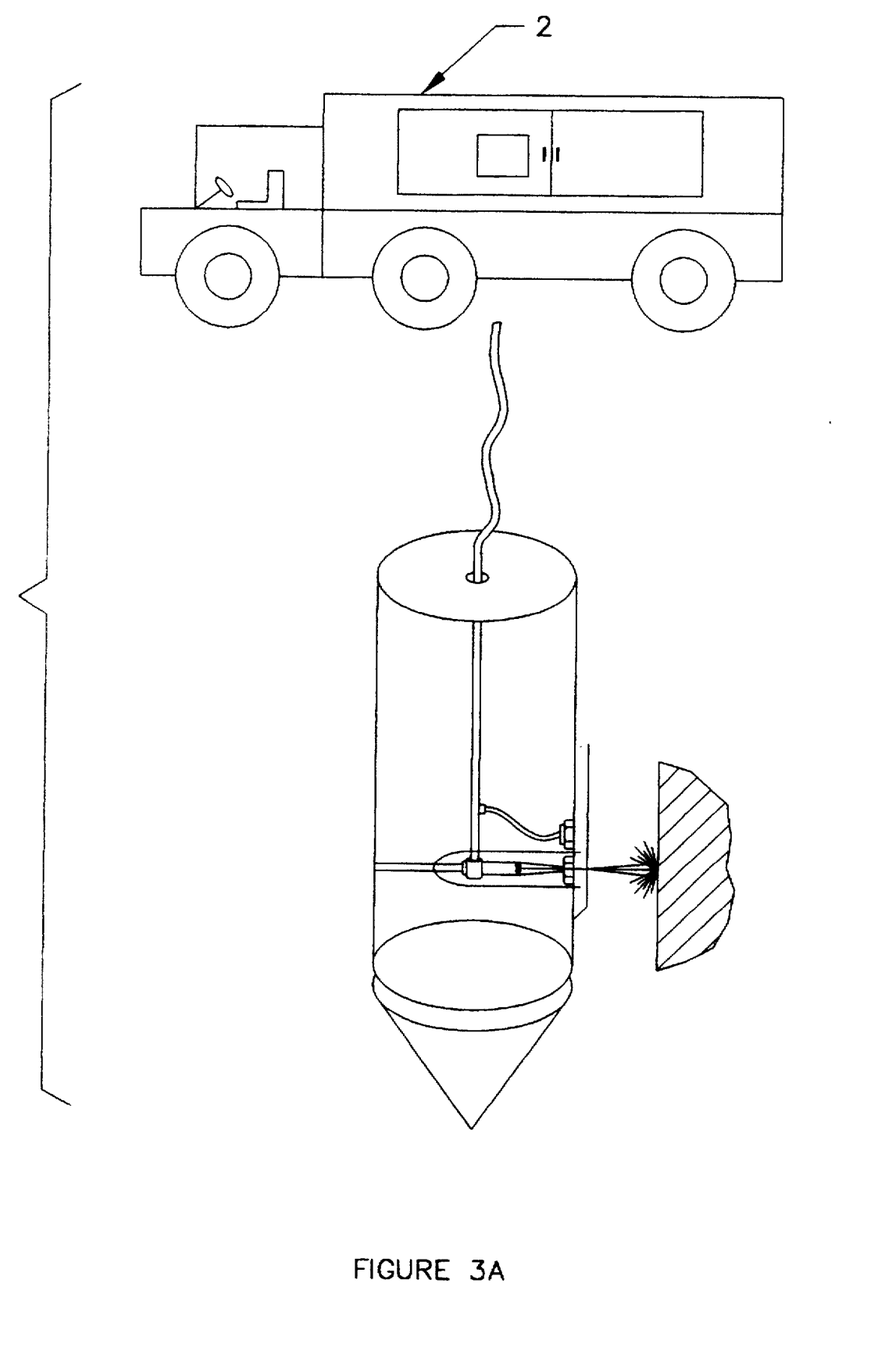
FIGS. 3A–3C show a subsurface solid analyzer according to a preferred embodiment of the invention.
Figure 3B:
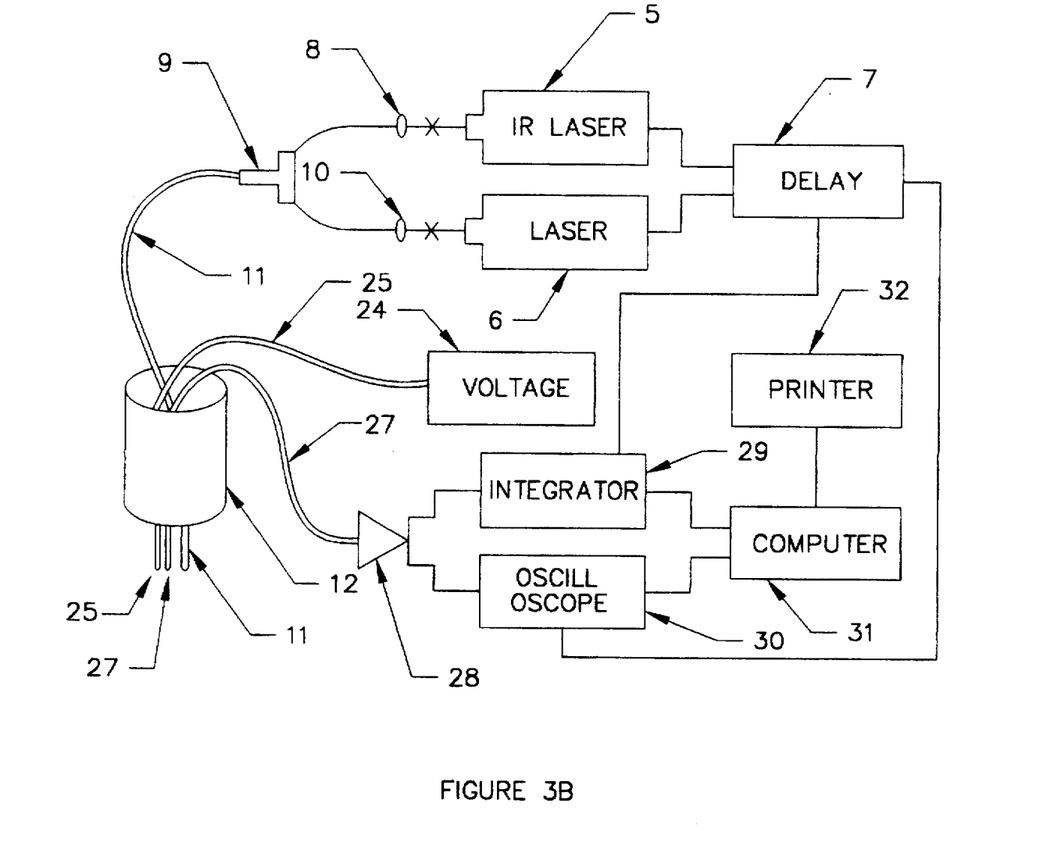
Figure 3C:
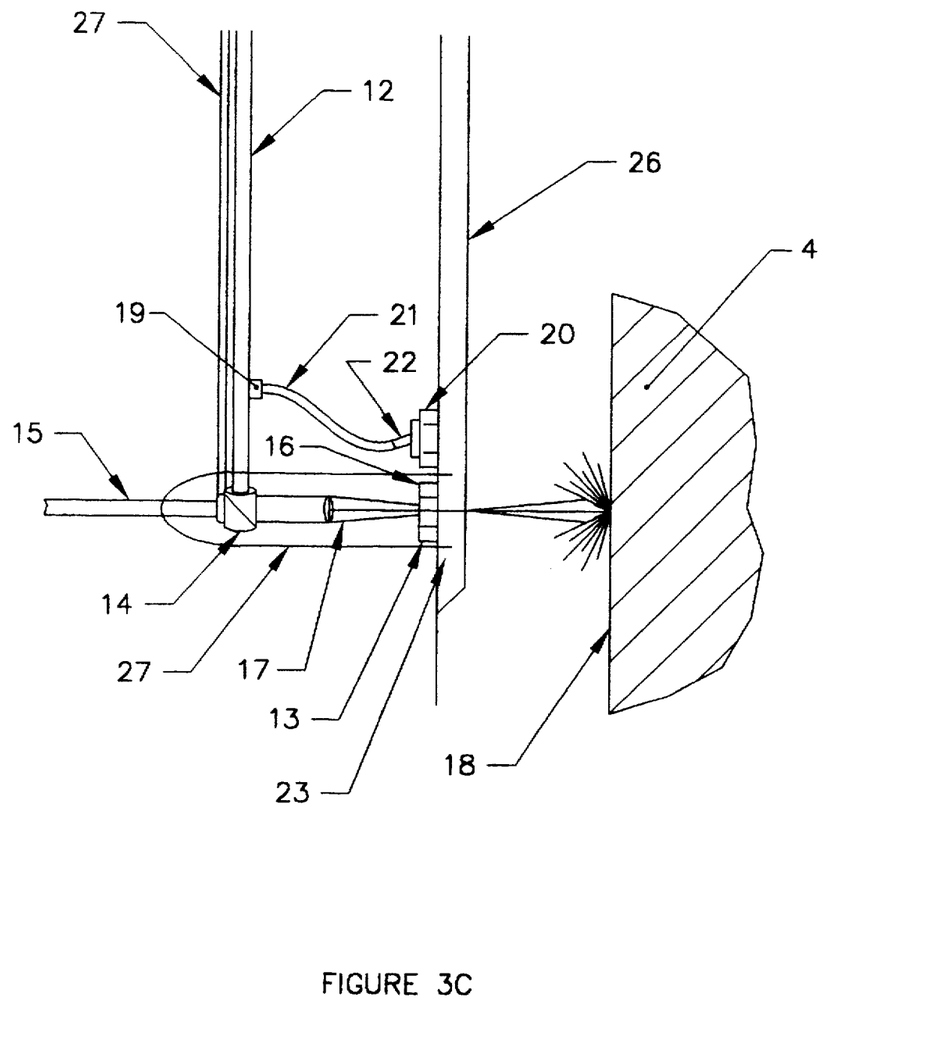

FIGS. 3A–3C together show a schematic of a subsurface soil analyzer 1 for potential energetic material contaminants according to the preferred embodiment of the present invention. The elements in FIGS. 3A–3C are not shown to scale. All of the components of the sensor are housed in truck 2 equipped with a hydraulic press to push or pull penetrometer 3 in or out of the ground 4. Infrared laser 5 is used to decompose the energetic material imbedded in the soil, yielding NO, while visible-wavelength laser 6 is used to ionize the NO by (2+2) resonance-enhanced multiphoton processes. Delay generator 7 time-delays the outputs from the two lasers; in other words, the two lasers produce their outputs at different times. The infrared laser beam is directed into lens assembly 8 which collimates it into one of the input ends of fiber optic "T" coupler 9. Similarly, the other laser beam is directed into the other input end of the fiber optic "T" connector via lens 10. The output end of the "T" connector is coupled to fiber optic 11 enclosed in flexible cable 12 which connects to cone penetrometer 3. The laser beams are transmitted inside the penetrometer through optical fiber cable 11 and redirected to optical port 13 near the penetrometer's cone head 3a by turning prism 14 mounted on post 15. A mirror can be used in place of the prism. The optical port 13 contains sapphire or diamond window 16. Lens 17 is used to collimate the exser beams. The IR radiation exits optical port 13 and impinges on surface 18 of the soil to be tested. Alternatively, the IR laser beam can be decoupled from the visible laser beam by frequency separator 19 and directed to optical port 20 via fiber optic cable 21 and optical mount 22. Optional elements 19–22 are shown in dashed lines. In the latter case, the infrared laser beam is not focussed. In either case, the contaminant energetic materials are decomposed yielding copious quantities of NO vapors. NO is then detected with a pair of stainless steel electrodes 23 mounted on the outside of optical port 13 by a (2+2) REMPI process using radiation near 452 nm from laser 6. The electrodes are powered by variable voltage supply 24 mounted onboard the truck via electrical wire 25 enclosed in flexible cable 12. Element 26 is a sacrificial shield which protects the electrodes as the penetrometer is pushed into the ground. Measurements are made on the penetrometer pull cycle once the sacrificial shield is released from the system. Alternatively, the electrodes 23 could be mounted inside the penetrometer near optical port 13 with the window 16 removed. The ion/electron signal is transmitted by an electrical wire 27 into the input of an amplifier 28 which converts the current to voltage. On-board the truck, the signal is sampled by boxcar integrator 29 or displayed in real-time on digital oscilloscope 30. Laptop computer 31 (or another suitable computing device) interfaced to boxcar 29 and oscilloscope 30 is used for data acquisition and analysis. For hard copies of the data, printer 32 is connected to the computer.

Figure 4:
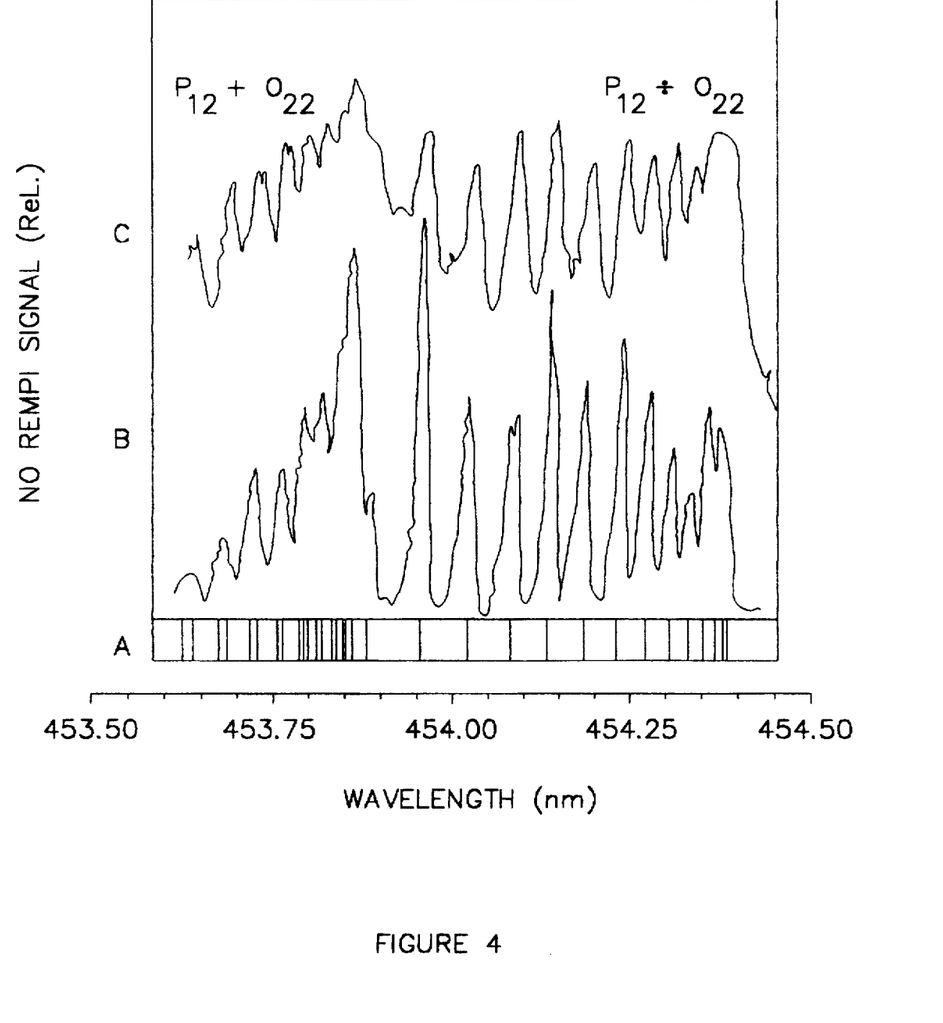
FIG. 4 shows calculated and observed REMPI spectra of NO.

Presented in FIG. 4 are calculated (A) and observed (B and C) REMPI spectra of NO in the region of 453.5–454.5 nm. The calculated line spectrum was obtained using spectroscopic data reported by G. Herzberg in *Molecular spectra and molecular structure: I spectra of diatomic molecules*, Van Nostrand: Princeton, 1950, while the observed spectra were recorded with a prototypical system at 100 Torr (B) and 760 Torr (C) using 0.1%. NO. The two bands displayed in the spectra are assigned to the NO $(P_{12}+O_{22})$ and $(P_{12}+O_{22})$ transitions which arise from two-photon quantum selection rules of NO (A–X) transitions. It should be noted that these bands are not observed near 226 nm, the origin of the NO (A–X) (0,0) band. As shown in FIG. 4, the calculated line spectrum predicts all of the observed NO spectral features. The spectral resolution at 760 Torr is less than that at 100 Torr as a result of collisional broadening, but is sufficient to differentiate individual rotational lines in the spectra.

Figure 5:
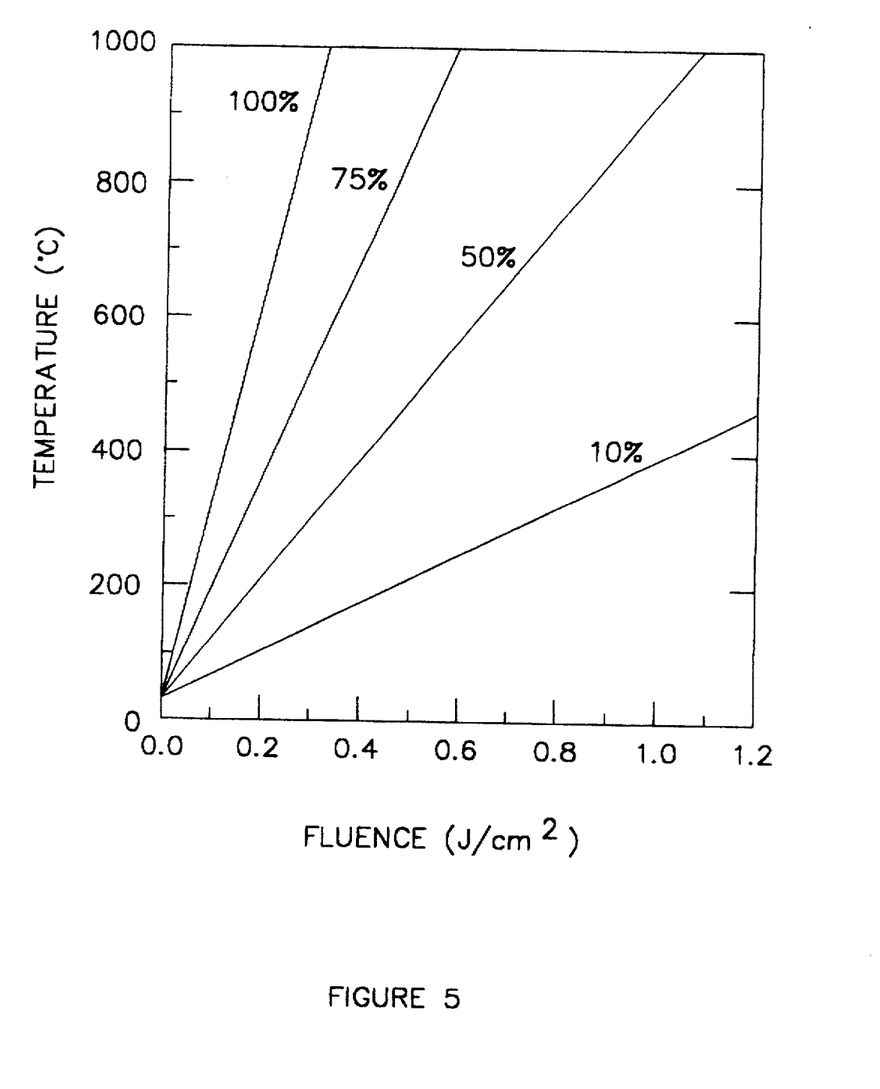
FIG. 5 shows plots of a surface temperature of sandstone with trace RDX and HMX.

FIG. 5 shows plots of the surface temperature of sandstone with trace RDX and HMX as a function of laser fluence for various percentages of absorbed laser radiation. The plots were obtained using equation (1). As shown in FIG. 5, if only 10% of the laser beam is absorbed by the materials, a fluence of approximately 1.2 J/cm$^2$ is required to increase the surface temperature to over 400° C. in 1 microsecond. This temperature is sufficient to decompose both RDX and HMX into NO and other products as discussed in the earlier section of this disclosure. A fluence of 1.2 J/cm$^2$ is readily obtained from commercially available infrared lasers.

While a preferred embodiment of the invention has been set forth, those skilled in the art who have reviewed this specification will readily appreciate that other embodiments within the scope of the invention can be achieved. For example, components disclosed as being in the truck can instead be located in the cone penetrometer. Therefore, the invention should be construed as being limited only by the appended claims.

What is claimed is:

1. A method for detecting and monitoring subsurface soil potentially contaminated with trace energetic materials selected from the group consisting of organic NO- and NO2-containing species in real time and in situ, the method comprising:

(a) driving a penetrometer into the subsurface soil;

(b) producing first and second time delayed laser pulses from first and second laser sources, respectively and directing the time delayed laser pulses out of the penetrometer onto the subsurface soil so as to decompose the energetic materials via the first laser pulses to produce a decomposition product and to ionize the; decomposition product via the second laser pulses to produce ions;

(c) detecting the ions to produce a signal representing a concentration of the ions; and (d) determining a presence and concentration of the energetic material in accordance with the signal.

2. A method as in claim 1 wherein the decomposition product comprises NO, and step (b) comprises ionizing the NO by a (2+2) resonance-enhanced multiphoton ionization process via an A electonic state.

3. A method as in claim 2, wherein the NO is ionized from a ground ro-vibrational state.

4. A method as in claim 1, wherein the decomposition product comprises NO and step (b) comprises ionizing the NO by a (2+2) resonance-enhanced multiphoton ionization process via a B electronic state, in lieu of an A electronic state.

5. A method as in claim 1, wherein the decomposition product comprises NO and step (b) comprises ionizing the NO by a (2+2) resonance-enhanced multiphoton ionization process via a C electronic state, in lieu of an A electronic state.

6. A method as in claim 1, wherein the decomposition product comprises NO and step (b) comprises ionizing the NO by a (2+2) resonance-enhanced multiphoton ionization process via a D electronic state, in lieu of an A electronic state.

7. A method as in claim 1, wherein step (c) comprises detecting the ions by multiphoton ionization spectroscopy.

8. A method as in claim 7, wherein the trace energetic materials comprise volatile organic materials.

* * * * *